(12) United States Patent
Weber et al.

(10) Patent No.: US 9,737,431 B1
(45) Date of Patent: Aug. 22, 2017

(54) WRIST-FOREARM-ELBOW ANTI-ROTATION ORTHOSIS

(71) Applicant: WEBER ORTHOPEDIC INC., Santa Paula, CA (US)

(72) Inventors: James J. Weber, Santa Barbara, CA (US); Michael Behrman, Santa Barbara, CA (US); John Hely, Roanoke, TX (US); Martha Ortega, Oxnard, CA (US)

(73) Assignee: Weber Orthopedic, Inc., Santa Paula, CA (US)

( * ) Notice: Subject to any disclaimer, the term of this patent is extended or adjusted under 35 U.S.C. 154(b) by 71 days.

(21) Appl. No.: 14/825,076

(22) Filed: Aug. 12, 2015

Related U.S. Application Data

(63) Continuation-in-part of application No. 14/341,654, filed on Jul. 25, 2014.

(60) Provisional application No. 61/883,826, filed on Sep. 27, 2013.

(51) Int. Cl.
   *A61F 5/00*  (2006.01)
   *A61F 5/01*  (2006.01)
   *A61F 5/30*  (2006.01)

(52) U.S. Cl.
   CPC .............. *A61F 5/0118* (2013.01); *A61F 5/30* (2013.01)

(58) Field of Classification Search
   CPC ........... A61F 5/0118; A61F 5/30; A61F 5/013
   USPC ................ 602/20, 4; 128/178; D24/190–192
   See application file for complete search history.

(56) References Cited

U.S. PATENT DOCUMENTS

| | | | |
|---|---|---|---|
| 2,655,916 A * | 10/1953 | Timmins ............... | A61F 5/0585 602/4 |
| 3,678,926 A * | 7/1972 | Strittmatter ......... | A61F 5/05858 5/647 |
| 4,235,228 A | 11/1980 | Gaylord et al. | |
| 4,598,702 A * | 7/1986 | Lilla ..................... | A61F 5/3738 602/4 |
| 7,314,457 B2 | 1/2008 | Reaux | |
| 7,329,229 B2 | 2/2008 | Scheinberg | |
| 7,988,653 B2 | 8/2011 | Fout | |
| 8,480,502 B2 * | 7/2013 | Korte .................. | A63B 69/0046 473/62 |
| 2004/0002671 A1 | 1/2004 | Reaux | |
| 2004/0215119 A1 * | 10/2004 | Avon .................... | A61F 5/3738 602/4 |
| 2013/0211304 A1 | 8/2013 | Romo | |

FOREIGN PATENT DOCUMENTS

EP            0439552 B1       3/1995

* cited by examiner

*Primary Examiner* — Kim M Lewis
(74) *Attorney, Agent, or Firm* — Paul Y. Feng; One LLP

(57) ABSTRACT

A wrist-forearm-elbow anti-rotation support system and process that do not require a hardenable material. The system includes an orthopedic support such as a wrist-hand orthosis, wrist-hand-thumb orthosis, joined to a bottle-shaped forearm wrap with opposed flaps formed into a clamshell. Proximal elbow flaps include a center elbow region that extends from the proximal end of the forearm wrap. Attaching straps and/or cross straps extending from the proximal elbow flaps attach to the forearm flaps and may crisscross. Hook and loop fasteners extending from the distal edge of the forearm wrap attach the forearm flaps.

17 Claims, 15 Drawing Sheets

WRIST-FOREARM-ELBOW ANTI-ROTATION ORTHOSIS

CROSS-REFERENCE TO RELATED APPLICATIONS

This application is a continuation-in-part (CIP) of co-pending patent application Ser. No. 14/341,654, filed Jul. 25, 2014, which claims priority to U.S. provisional patent application No. 61/883,826, filed Sep. 27, 2013, the contents of all of which are incorporated by reference.

FIELD OF THE INVENTION

The present invention relates to an orthopedic brace. In particular, the present invention relates to wrist-forearm-elbow anti-rotation orthosis to immobilize the elbow and wrist or like injuries.

BACKGROUND

A "Sugar Tong" splint is a splint that is used to immobilize both lower arm bones so there is no motion relative to themselves—in other words an anti-rotation splint of the forearm. The indications for these types of splints are: distal radius or ulna fractures, and fractures of the wrist and elbow. Advantages of the splint are that it greatly restricts rotation of the forearm—supination and pronation of the forearm—while allowing for swelling and providing excellent strength. The name of the splint is derived from its appearance which is reminiscent of sugar tongs used to pick up cubes of sugar.

One of the disadvantages of this conventional sugar tong splint is the time involved and skilled technique required to properly make the splint and apply it to the patient. For example, each sugar tong splint is custom made to fit each patient using components such as adhesive tape, gauze, strips of casting tape, and bandage, which then must be cut to size with scissors and pieced together. Strips of splint or casting material must be selected for the correct dimensions and its length cut to match the patient's arm, moistened sufficiently but not overly, applied precisely to the patient's wrist/forearm/elbow regions, leaving gaps in key areas to accommodate for swelling. The technician must also carefully wrap and smooth out folds and creases, etc., to ensure efficacy and comfort for the patient.

The splint typically includes or is impregnated with hardenable material such as plaster, fiberglass, resin, etc. Thus, applying the splint to the patient correctly and doing so before the hardenable material begins to set, cure, or harden involves a time constraint. Due to this time constraint, once the hardenable material sets, cures, or hardens, no further adjustments can be made to accommodate for increase or decrease in swelling, to increase range of motion of the injured joint, to enable exercising the injured limb, to remove creases or smooth out bunched material, etc.

Thus, having an off-the-shelf bracing system ready to go offers greater ease and flexibility to doctors, cast technicians, and therapist to treat arm fractures more efficiently and effectively at the hospital, clinical, and therapeutic levels.

SUMMARY OF THE INVENTION

The present invention in a preferred embodiment is directed to an elbow-forearm anti-rotation support system that does not use hardenable material. As seen in FIG. 1, a preferred embodiment sugar tong forearm brace comprises a forearm wrap 1 that may or may not be split down the center with stretch material and secured with flexible fabric 1a. The forearm wrap 1 is made of either a flexible semi-rigid material, or a soft pliable material and has two opposed flaps or panels 9. The distal edge of the forearm wrap 1 has connective means 2 (e.g., hook and loop fasteners, or like attachments) to secure the sugar tong brace to any of the following: (a) wrist-hand orthosis shown in FIG. 1; (b) wrist-hand-thumb orthosis (thumb spica splint); (c) short arm cast; (d) thumb spica cast; or (e) similar orthopedic brace, support, splint, or cast.

In the preferred embodiment, the proximal end of the forearm wrap 1 is tapered or bottlenecked to seat at the elbow of the patient, with proximal flaps 3 that come up the back of the upper arm and wrap around the sides of the back of the lower part of the upper arm. Straps 4 are connected to the end of each flap 3 (and can be connected pivotally, they are sewn in this prototype) and cross over the top of the forearm and secure on opposite sides of the forearm with hook means 5. An inner removable malleable aluminum stay 6 with attachment means at each end 7 is secured to the inside back portion of the proximal wrap flaps 3. The malleable aluminum strip is designed to be shaped around the back just above the elbow. A closure strap 8 is also attached to the forearm wrap 1 to assist with initial application. Removable lateral and medial stiffeners are placed inside of pockets that are sewn to the outside of forearm wrap 1, for increased stiffness and support.

In an alternative embodiment, a one-piece wrist-forearm-elbow anti-rotation support system that does not include a hardenable material is contemplated. The system comprises a forearm wrap having a proximal end and a distal end, the forearm wrap including two opposed, first and second forearm flaps wrapped into a clamshell form, wherein the flaps approach each other. The system includes a humeral connection having a proximal section and a distal section, wherein the distal section connects to the clamshell forearm wrap. Proximal elbow flaps extend from the proximal section, and first and second straps extend from the proximal elbow flaps that attach to the first and second forearm flaps. A web space closure disposed at the distal end of the forearm wrap extends from the first forearm flap to the second forearm flap.

DETAILED DESCRIPTION OF THE PREFERRED EMBODIMENTS

Conventional sugar tong casts or splints are used to stabilize injuries of the forearm and wrist by preventing forearm rotation and wrist motion. These casts and splints may further be used to maintain alignment of broken bones or to protect a patient's forearm or wrist after surgery. A conventional sugar tong cast is made from plaster, fiberglass, or like hardenable splinting material, usually in the form of 3-inch or 4-inch wide strips. A skilled technician applies the strips to the patient with his or her palm down on the forearm behind the humerus and back to the top of hand like a stirrup. The present invention system completely replaces the conventional sugar tong cast that must be custom made from strips impregnated with hardenable material.

Figure 1:
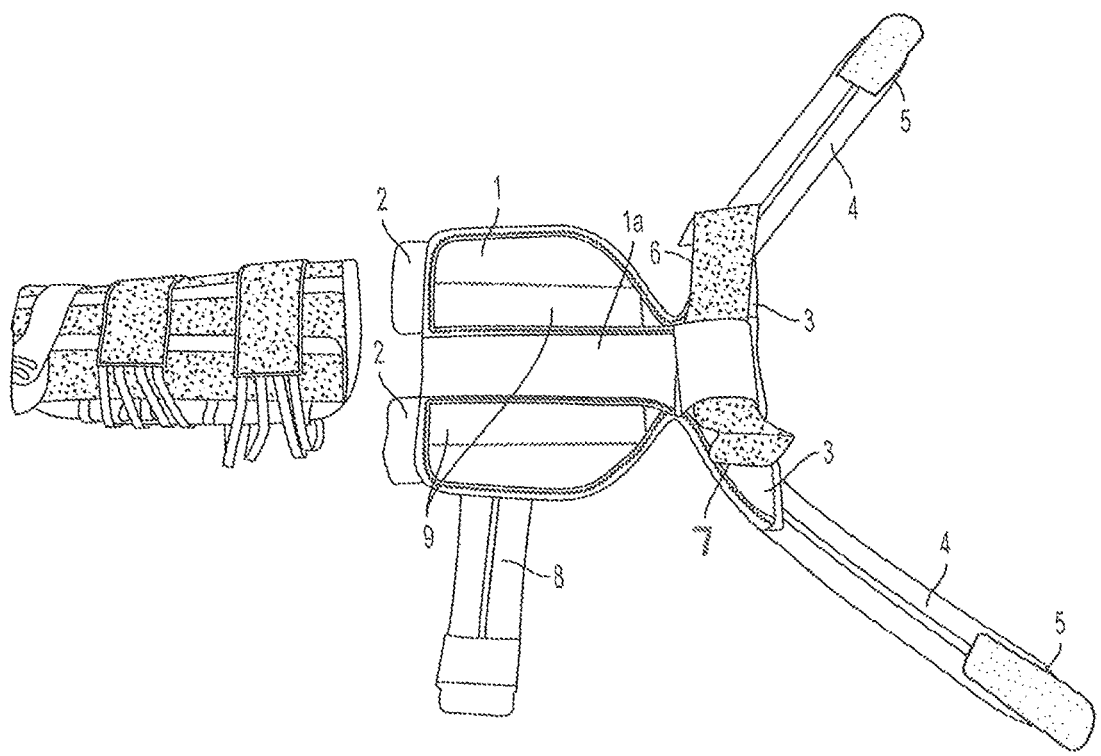
FIG. 1 is a plan view of an elbow-forearm anti-rotation support system.

FIG. 1 is a preferred embodiment of the present invention an elbow-forearm anti-rotation support system, also known as a sugar tong brace. In particular, the present invention in the preferred embodiments is directed to an orthopedic support such as a wrist/hand, or wrist/hand/thumb forearm elbow orthosis joined to a forearm-elbow portion with minimal to no relative rotation therebetween. The forearm-elbow portion of the brace may be further used in concert with a short arm cast or splint, or thumb spica cast or splint. The preferred embodiment shown in FIG. 1 is a sugar tong forearm brace used optionally in combination with a wrist-hand orthosis.

Figure 5A:
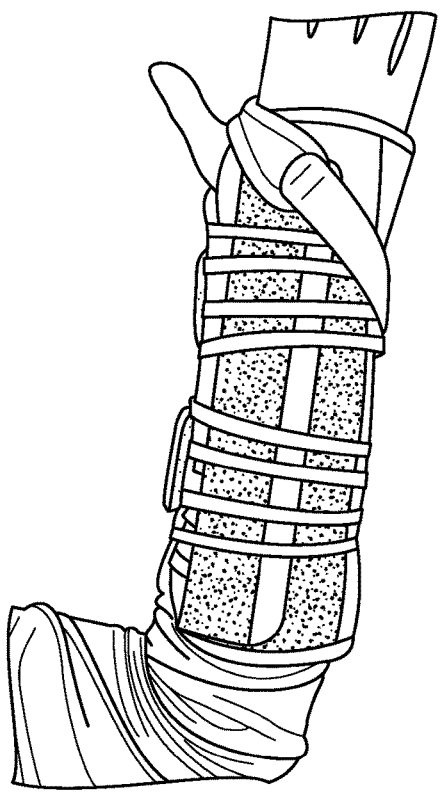
FIGS. 5A and 5B are side elevational views of the lateral and medial sides, respectively, of the wrist-hand orthosis worn on a patient's arm.
Figure 5B:
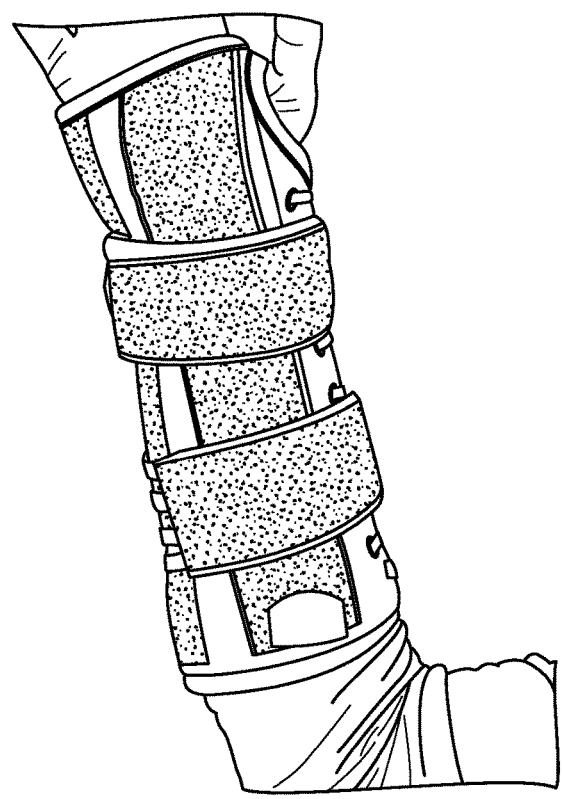

FIGS. 1, 5A, and 5B show an exemplary embodiment orthopedic support, here, a wrist-hand orthosis. It is made from a flexible holder to receive the patient's wrist, and has two flaps that close toward one another to secure the holder about the patient's wrist and forearm. Tightening strands, straps, or laces pass through the edges of the flaps to cinch up the two flaps, and anchoring flaps at the collective ends of the laces attach to the brace once the flaps are tightened. Another strap extends over the base of the thumb as with a thumb spica splint. The exterior of the flaps is made of a UBL (unbroken loop) or like material for easy attachment for hook and loop fasteners or the like.

In the embodiment shown in FIGS. 1, 5A, and 5B, the wrist-hand orthosis connected to the forearm wrap 1 may be of the type disclosed in, for example, U.S. Pat. No. 6,893,410 (Hely) and U.S. Pat. No. 6,960,176 (Hely et al.), which contents are incorporated by reference. Aside from the wrist-hand orthosis of FIGS. 1, 5A, and 5B, other orthopedic supports, braces, splints, are contemplated, such as: a wrist cast, short arm cast, thumb spica cast, wrist-hand orthosis, or wrist-hand-thumb orthosis known in the art; braces and splints disclosed on applicant's website: http://www.helyweber.com/index.php/upper-extremities/wrist-hand-a-thumb; or, for example, U.S. Pat. Nos. 7,033,331; 7,056,298; 6,142,966; 7,278,980; 7,442,177; 7,455,650; 7,402,149; 7,276,039; and 7,713,223, the contents of all of which are incorporated by reference.

Figure 3:
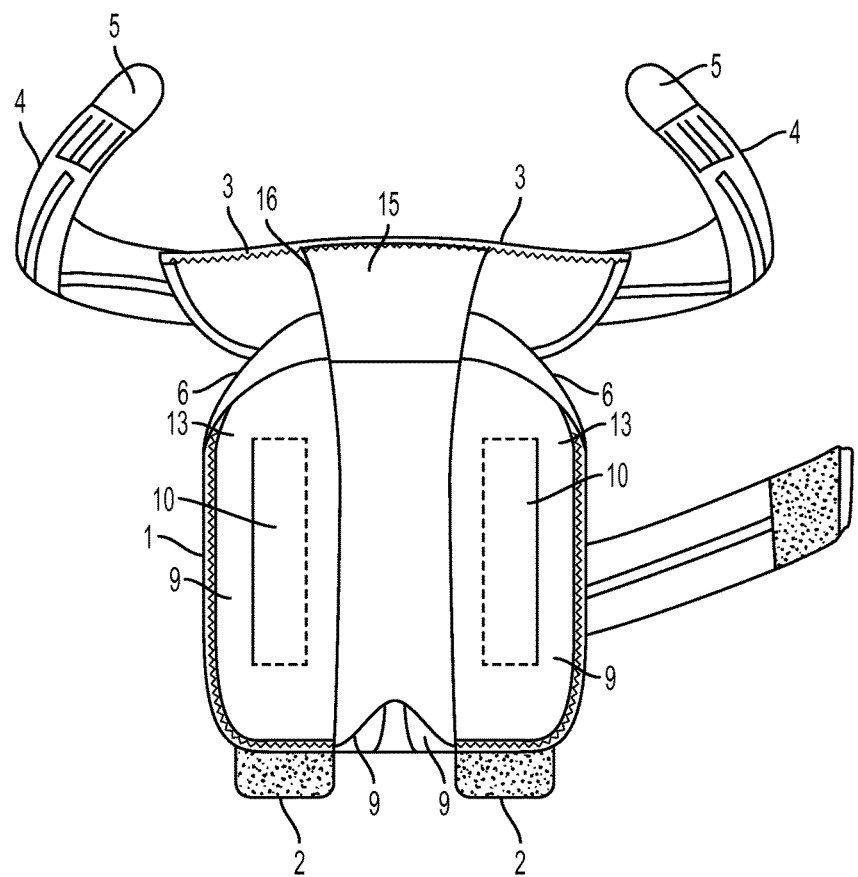
FIG. 3 is a plan view of a preferred embodiment sugar tong forearm wrap/portion.
Figure 10:
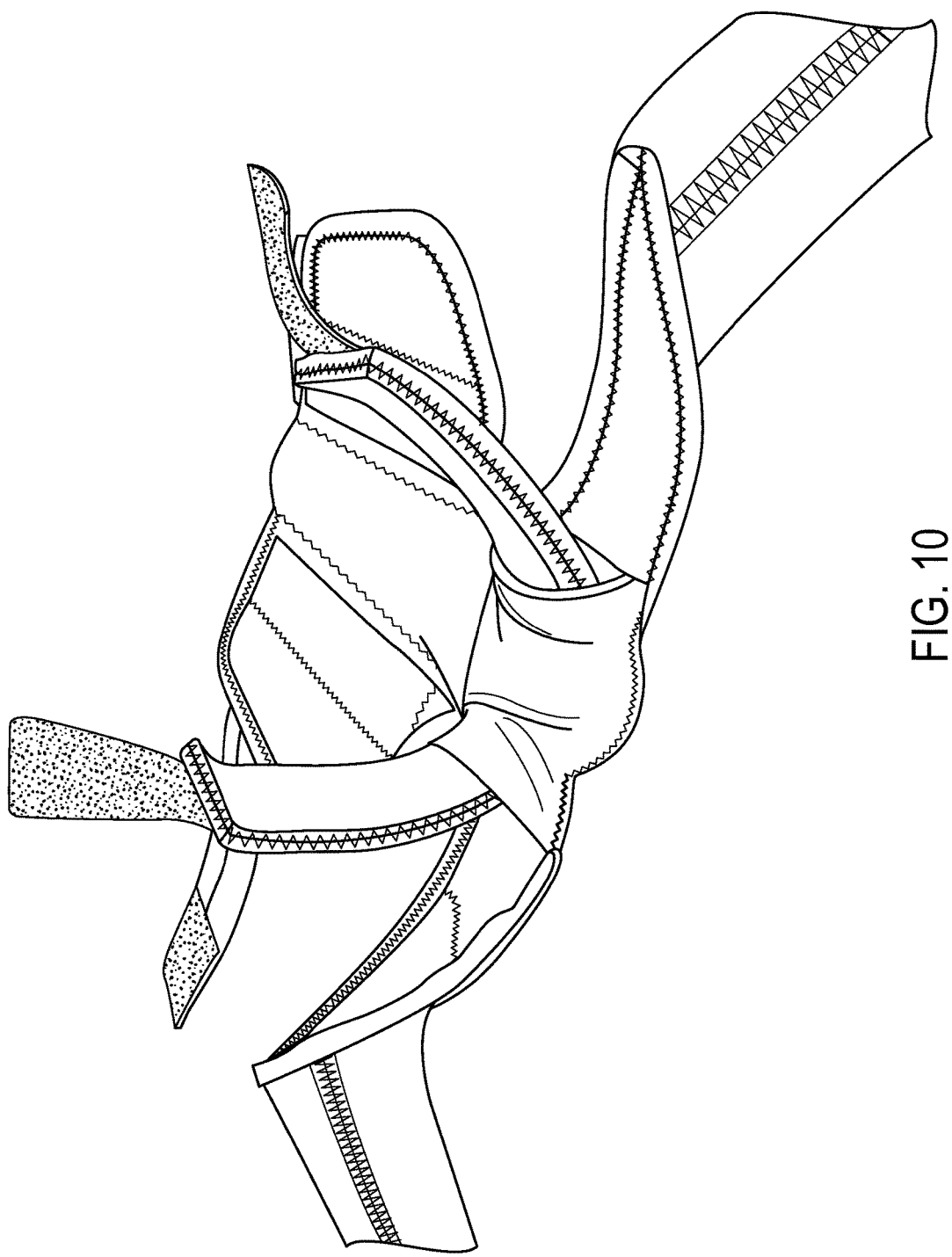
FIG. 10 is the preferred embodiment forearm wrap/portion showing the interior, with the first and second forearm flaps laid open, a U-shaped reinforcement stay, and proximal elbow flaps with straps laid open.
Figure 11:
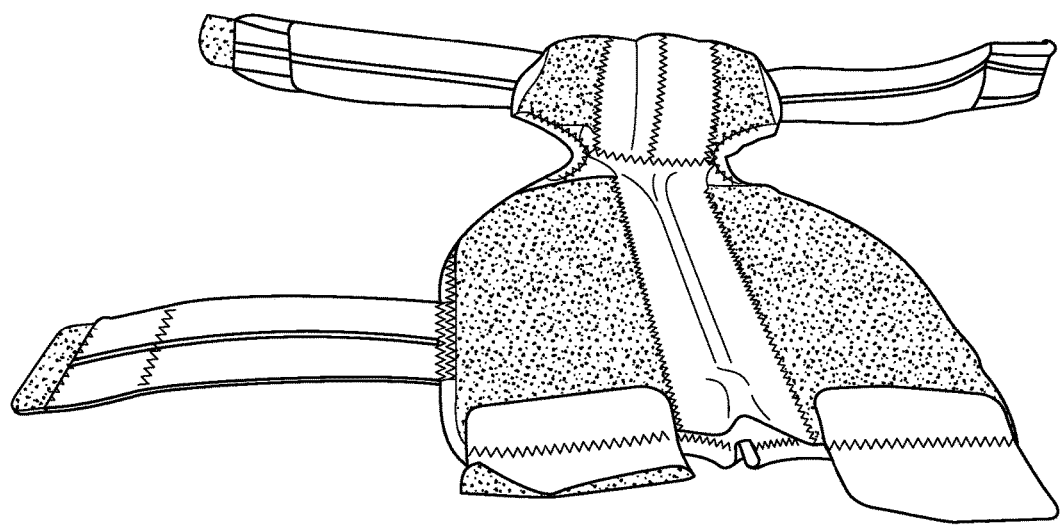
FIG. 11 shows the exterior of the forearm wrap/portion from FIG. 10.
Figure 12:
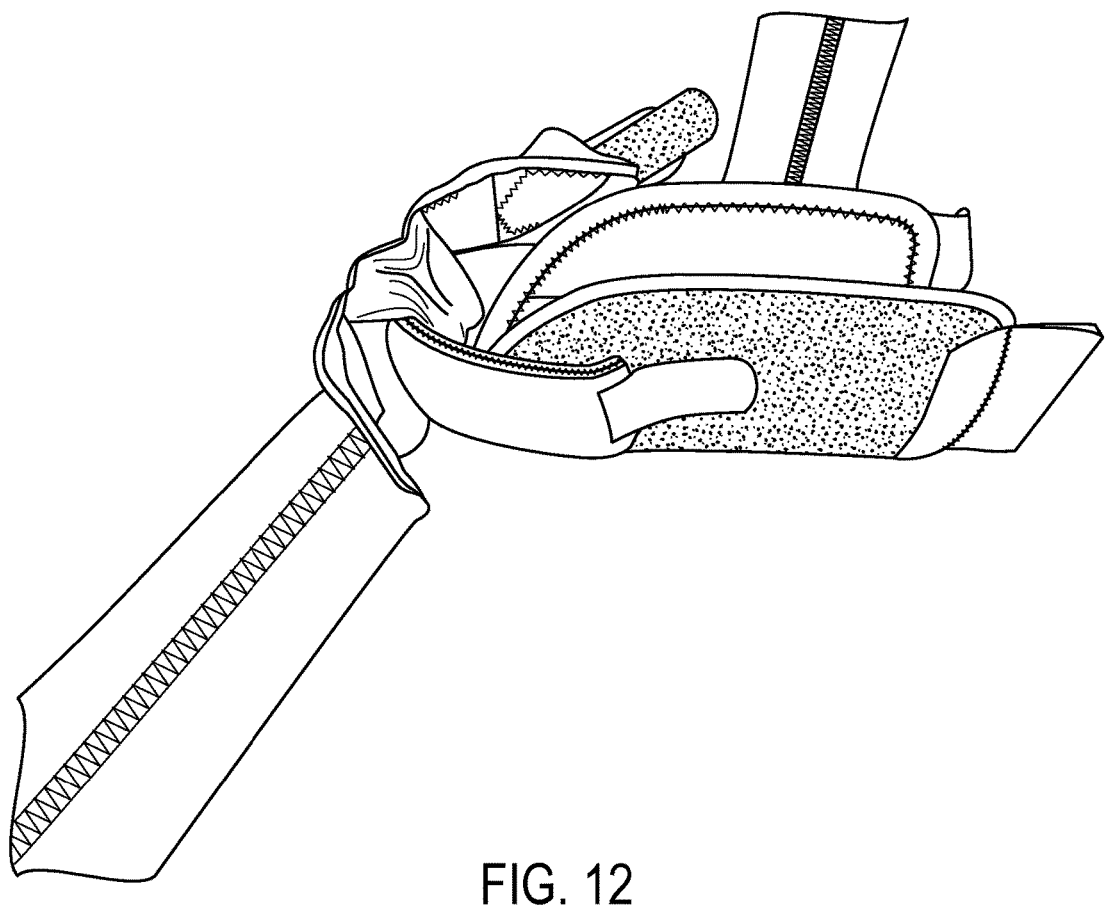
FIG. 12 is a side elevational view of the forearm wrap/portion from FIG. 10 with the proximal-elbow end on the left side and the distal-wrist end on the right side.

FIG. 3 is a plan view of a preferred embodiment sugar tong forearm brace depicted in FIG. 1, spread open exposing the interior, and oriented with the proximal or elbow end at the top and the distal or wrist end at the bottom. See also FIGS. 10-12 depicting the forearm wrap 1. The forearm wrap 1 has opposed flaps 9 that include elongated, padded panels shown in the opened position to receive the patient's forearm. The exterior of the panels/flaps 9 preferably include swatches or entirely of UBL or hook and loop fastener material (e.g., VELCRO®) to allow for attachment of VELCRO® hooks, straps, closures, clasps, buckles, claws, and the like. The two panels/flaps 9 are joined along one edge with one or more sheets of elastic fabric acting as an expandable hinge, and when applied, the opposite edges approach each other as in a clamshell leaving a split along the center with no gap, or there may be a gap at the split, or the edges may overlap and fully circumscribe the patient's forearm. In an alternative embodiment, the two flaps 9 may be formed into a cylinder, with elastic expansion regions, to fully circumscribe and enclose the forearm. The flaps 9 is preferably reinforced inside its outer shell with plastic, aluminum, steel, or like stiffener strips 10 for improved rigidity and support for the patient's injured forearm or wrist. The stiffener strips 10 may be stitched or embedded into the flaps 9, or the flaps may include user accessible pockets that receive the stiffener strips inside. An optional soft fabric lining 12 covers the seam between the opposed flaps 9. This minimizes abrasion to and improves the comfort for the wearer's forearm.

Preferred construction materials for the forearm wrap include rigid EVA (ethylene vinyl acetate) foam or other semi-rigid thermoplastic foam with fabric laminated to both sides of the flaps 9. The outer sides of the flaps 9 preferably have a UBL (unbroken loop) fabric that can receive VELCRO® hooks, or have added loops to make it VELCRO® hook receivable. There are optional pockets or compartments for one or more plastic or metal (aluminum) stiffeners 10 on one or both sides of the forearm wrap 1. The plurality of stiffeners 10 embedded within the flaps 9 preferably extend substantially the entire length of the forearm wrap 1. Thus, the stiffeners 10 further improve torsional stability of the forearm wrap 1 and of the entire brace.

In an alternative embodiment, the forearm wrap is made from a laminate with semi-rigid EVA foam on both sides of a malleable aluminum (aluminum in the middle to help retain a molded shape) with fabric on both outer sides of the EVA foam. So a laminated forearm wrap would be constructed with the following: fabric (UBL or other), EVA foam or other semi rigid foam, aluminum (malleable) strip(s), EVA foam or other semi rigid foam, fabric (UBL or other). The laminate panels may be glued, stitched, sewn, welded or likewise joined together.

Figure 4:
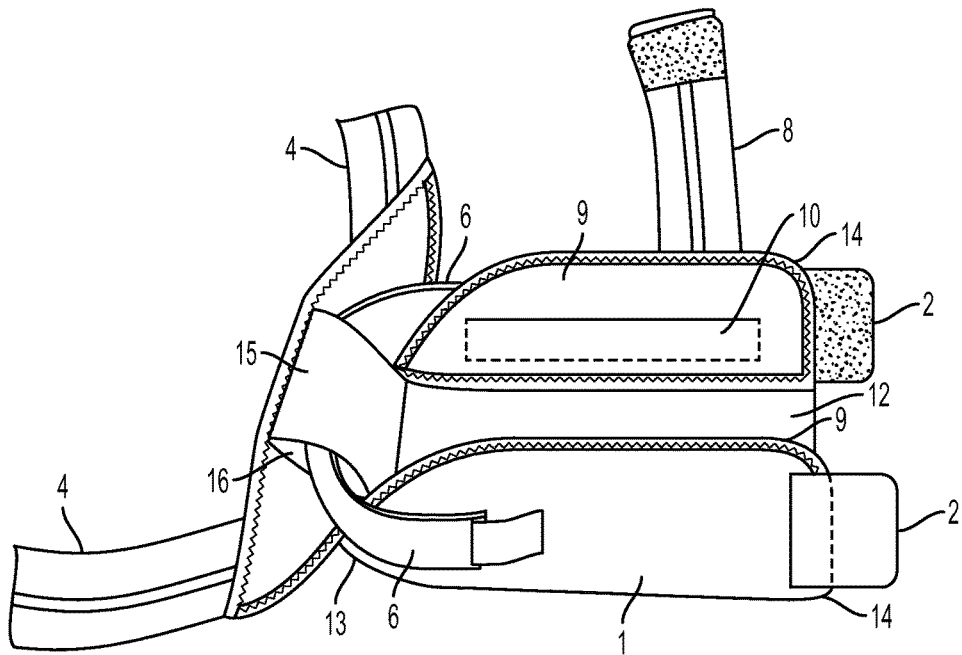
FIG. 4 is a side elevational view of the sugar tong forearm wrap/portion of FIG. 3.

FIG. 4 is a side elevational view of the forearm wrap 1 from FIGS. 1 and 3. As seen in FIGS. 1, 3 and 4, the flaps 9 of the forearm wrap 1 when laid open preferably form a bottleneck shape, with a tapered, narrower proximal edge 13 and a wider distal edge 14. The bottleneck shape minimizes bunching of flap material at the patient's elbow. The proximal edge 13 transitions into proximal flaps 3 that appear as wings extending from a center region covering the patient's elbow. Other shapes are contemplated for the forearm wrap, including a simple rectangle or like polygon.

The distal ends of the proximal flaps 3 each has a respective cross strap 4 used to wrap around the patient's forearm. When the brace is properly applied, the patient's elbow is covered by the soft fabric lining 12, then by the U-shaped reinforcement stay 6, then by the center region of the proximal flaps 3, all of which are secured in place by the cross straps 4. There may be fewer or more than the two cross straps 4 shown. The cross straps 4 are of sufficient length to attach to the exterior of the flaps 9 and/or attach to the wrist-hand orthosis (shown in FIG. 1). The cross straps 4 may have sufficient length to at least partially wind about the forearm wrap 1, further bolstering support for the patient's injured forearm and stabilizing the elbow. These straps use preferably VELCRO® hooks to attach to the forearm wrap 1 and/or the wrist-hand orthosis.

As shown in FIGS. 3 and 4, the sheet of soft fabric lining 12 extends over the center region of the proximal flaps 9 and forms a pocket 15 that received the patient's elbow therein. Further, the pocket 15 contains a passage 16 that allows an optional U-shaped reinforcement strip or stay 6 to loosely pass through it or be affixed to it, which passage 16 also helps keep the stay 6 in place. The U-shaped reinforcement stay 6 generally has a curved vertex extending into straight legs. The U-shaped reinforcement stay 6 is preferably made from a UBL fabric covering a fairly rigid metallic strip made from aluminum or steel, but plastic may be used too. The metallic strip is somewhat pliable for some level of customized fit for the patient's elbow region, but generally maintains its shape in use. It is fully enclosed or partially covered by a UBL soft fabric, padded, and is intended to provide support and protection for the patient's elbow. The distal ends of the straight legs of the U-shaped reinforcement stay 6 include optional hook and loop fasteners (e.g., VELCRO®) that attach to the exterior of the forearm panels/flaps 9.

An optional closure strap 8 extends from one of the forearm flaps 9 across the split or overlap and to the opposite forearm flap 9 to attach to the exterior thereof, preferably via hook and loop fasteners. More closure straps may be added for longer and larger sized forearm wraps. The strap may be replaced by or complemented by a plurality of laces extending from one flap over the split or gap and joined at the opposite end by a common attachment pad covered with VELCRO® hook fasteners.

All straps 4, 8 are preferably padded and made from soft fabric. Their lengths are preferably inelastic, but elastic straps that compress the forearm are contemplated in alternative embodiments. The ends of the straps 4, 8 are sewn to the base structure and the free distal ends of the straps are anchored to their intended attachment surface via hook and loop fasteners, but hooks, buckles, buttons, snaps, D-rings, laces and eyelets, and the like or any combination thereof, are contemplated.

Figure 6:
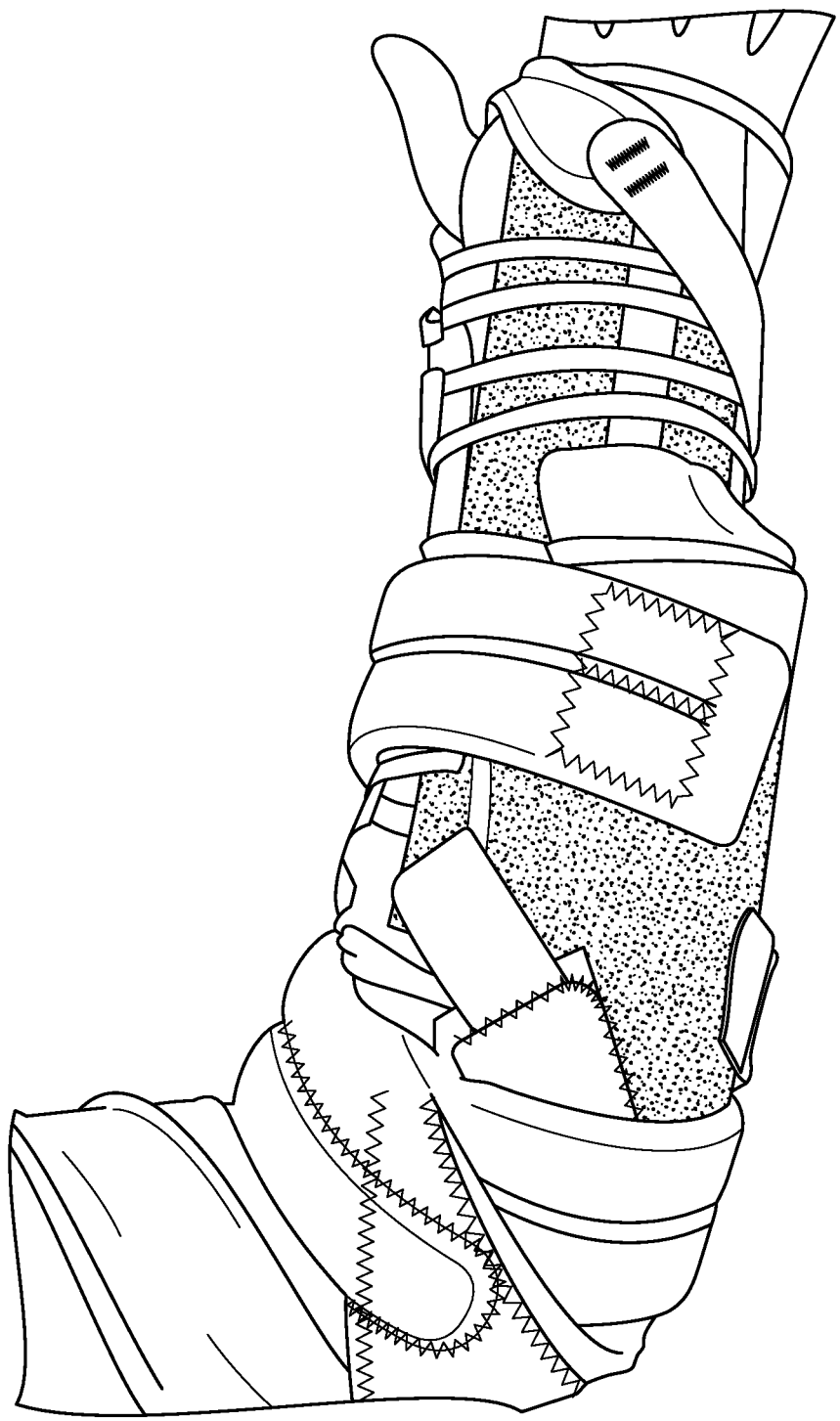
FIGS. 6 and 7 are side elevational views of the lateral and medial sides, respectively, of the wrist-hand orthosis and sugar tong forearm wrap/portion joined together as a system.
Figure 7:
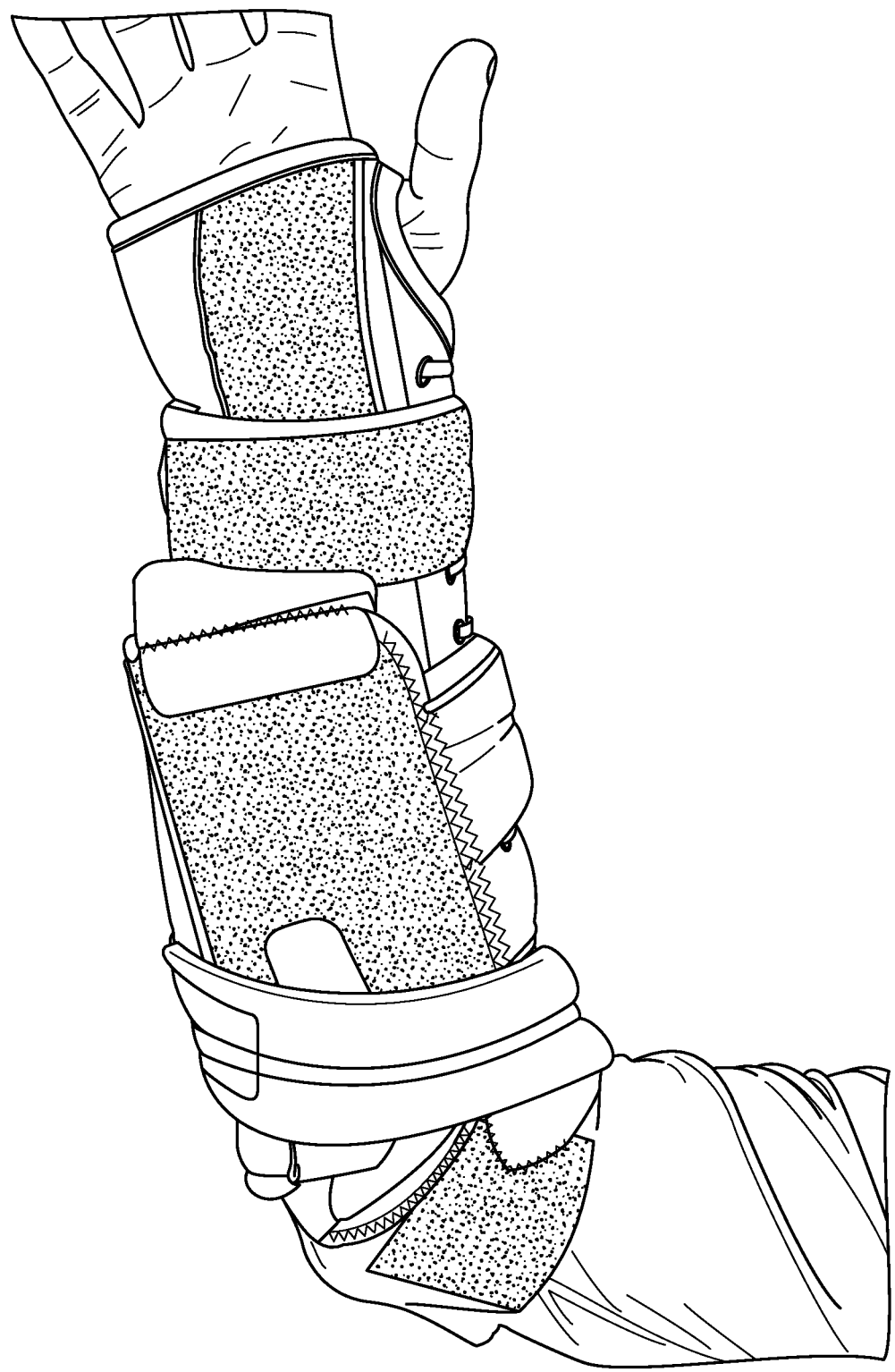
Figure 8:
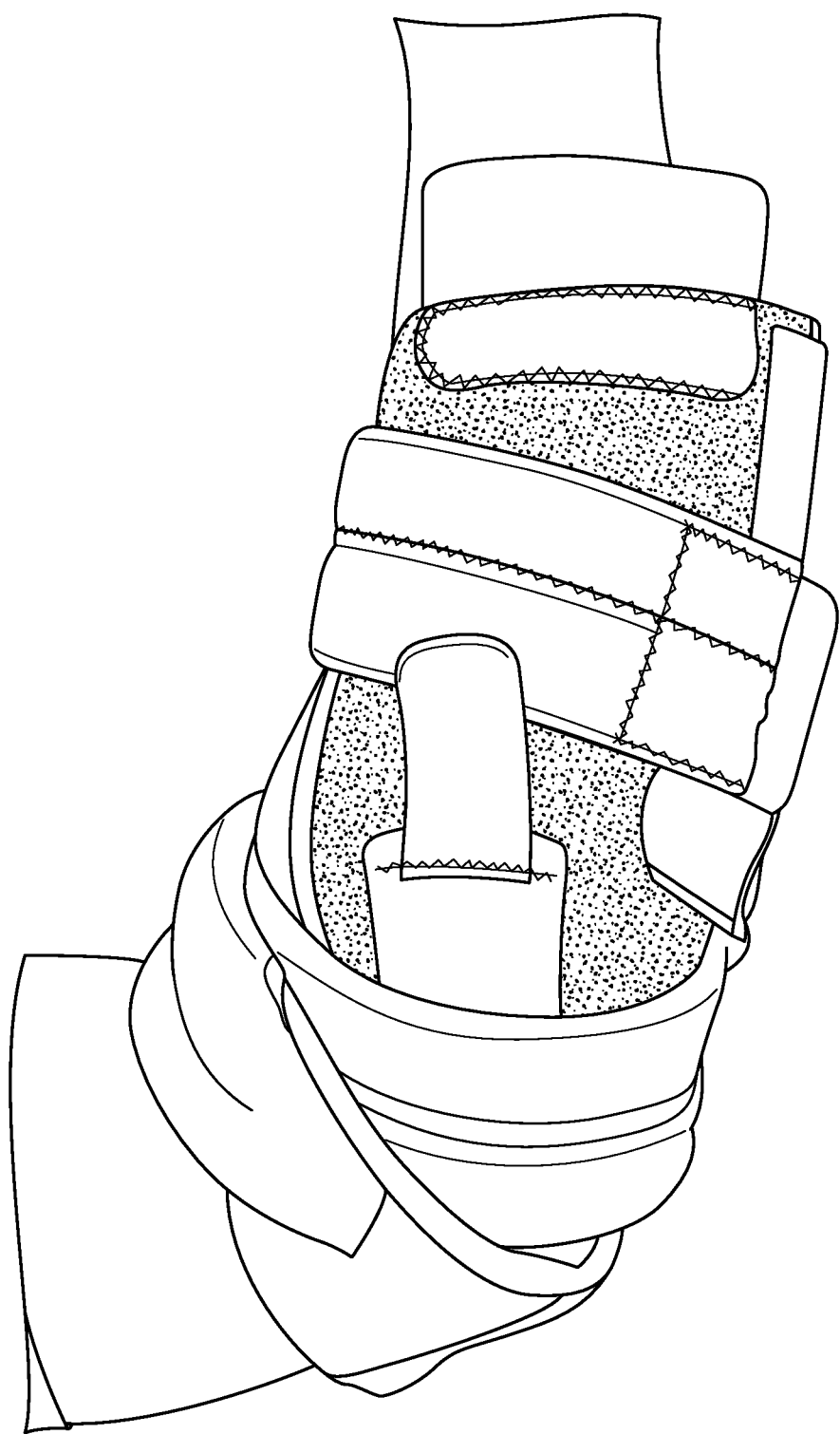
FIG. 8 is a lateral view of the preferred embodiment sugar tong forearm wrap/portion by itself.
Figure 9:
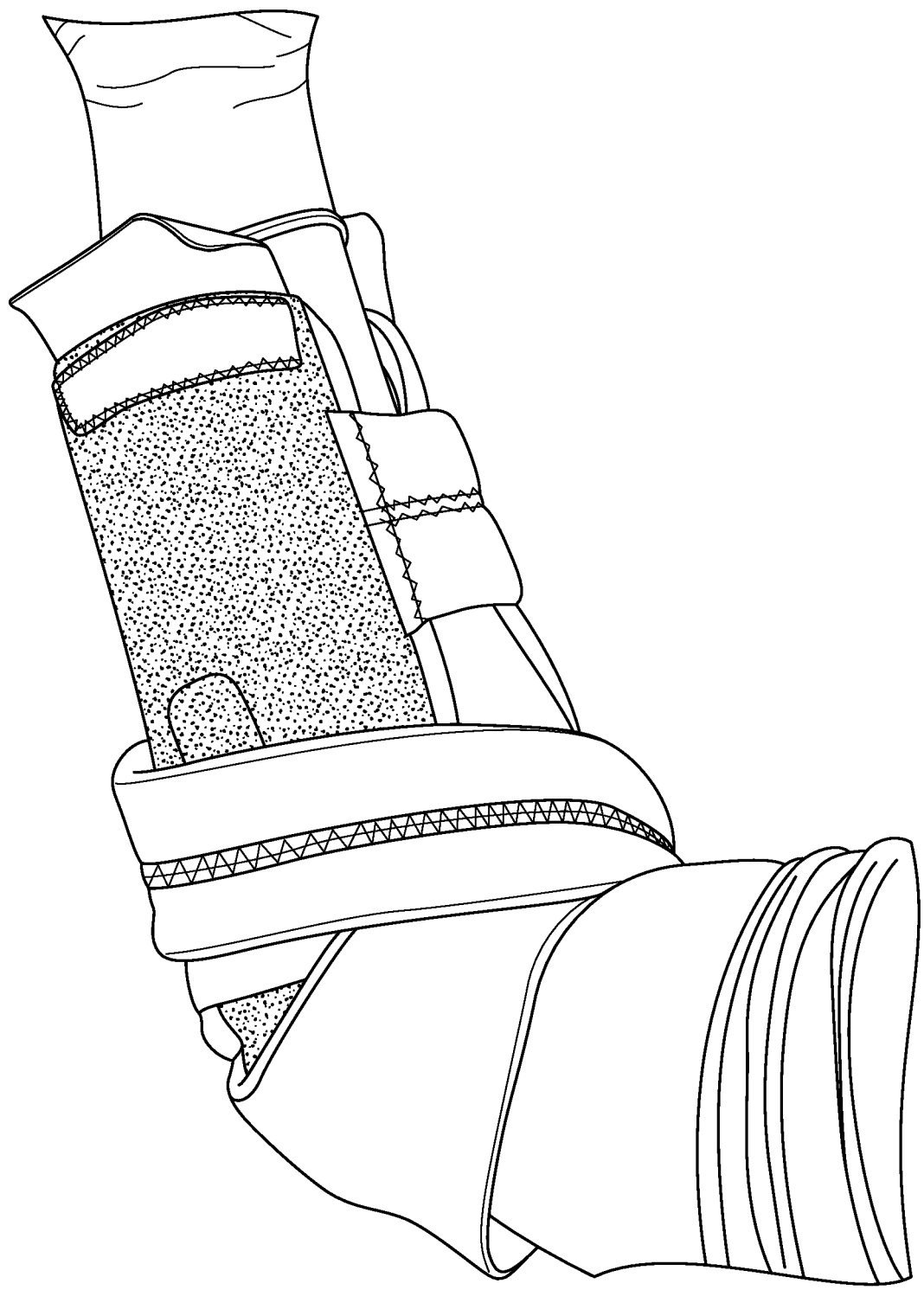
FIG. 9 is a medial view of the forearm wrap/portion from FIG. 8.

As seen in FIGS. 1, 3, 4, 8, and 9, the respective distal edges 14 at the distal end of the forearm flaps 9 preferably include anti-rotation connective means 2 used to join or attach the forearm wrap 1 to the orthopedic support, wrist-hand orthosis, cast, or splint being used (see FIGS. 6, 7). The connective means 2 are preferably two or more panels of VELCRO® hook fasteners that attach to the complementary hook and loop or UBL material or like receiving structure on the wrist-hand orthosis, cast, or splint. The connective means 2 are preferably of sufficient size to minimize the chance of accidental disconnection between the two braces.

Further, the anti-rotation connective means 2 should have sufficient purchase of the wrist-hand orthosis, cast, or splint to minimize relative rotation between the two braces. If hook and loop fasteners are used, they should preferably be large panels for a positive contact to the splint or cast that resists and immobilizes twisting in the patient's forearm and wrist. This feature thus limits the amount of forearm pronation or supination to help with rehabilitation. Instead of hook and loop fasteners, the connective means in alternative embodiments may be snaps, laces and eyelets, D-rings, hooks, zippers, buckles or catches with belts, and the like, or any combination thereof.

Beneficially, the preferred embodiments of the forearm wrap 1 and its components and attachments shown in FIGS. 3, 4, and 10-12, do not require any hardening material (e.g., plaster, resin, fiberglass, etc.) used in a traditional sugar tong cast to create the needed rigidity, anti-rotation, and support. Further, a high level or technician expertise is not required since customized taping and shaping are not required when using the present invention elbow-forearm anti-rotation support system.

FIGS. 2A-2F show a preferred application procedure for the present invention sugar tong brace to a patient's injured forearm.

Figure 2A:
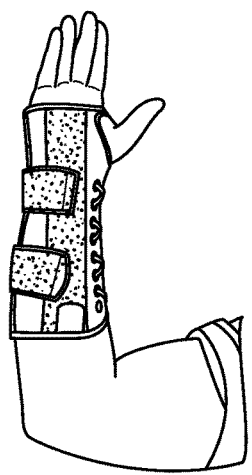
FIGS. 2A-2F show application of the system from FIG. 1 to a patient's arm.

FIG. 2A. Step 1—Apply an orthopedic support such as a forearm cast with a thumb spica cast or thumb spica wrist splint to the patient's forearm and hand.

Figure 2B:
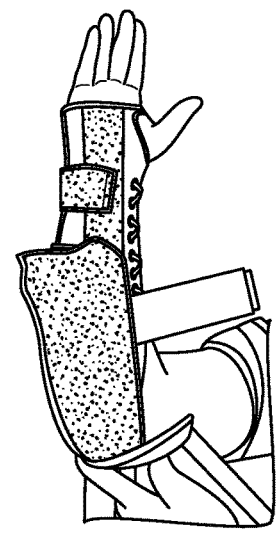

FIG. 2B. Step 2—The patient's forearm is placed inside the forearm wrap. The patient's elbow is seated in the U-shaped reinforcement stay, and the two ends of the stay are attached to the exterior of the wrap using VELCRO® hooks. The stay has an internal U-shaped stiffener that is generally stiff but still somewhat malleable and is adjusted for a customized fit to the patient's elbow.

Figure 2C:
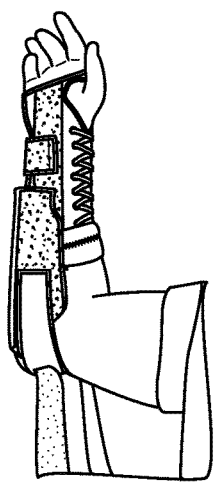

FIG. 2C. Step 3—Attach the anti-rotation connective means of the forearm wrap to the forearm cast or wrist splint, and secure the two sides of the forearm wrap with the closure strap.

Figure 2D:
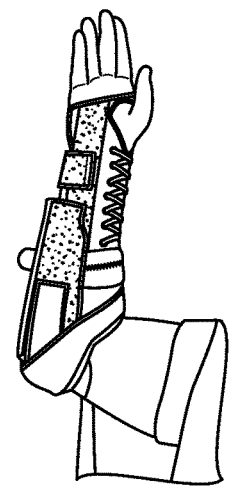

FIG. 2D. Step 4—Secure a first cross strap of the forearm wrap across top of forearm and connect to the forearm cast or wrist splint.

Figure 2E:
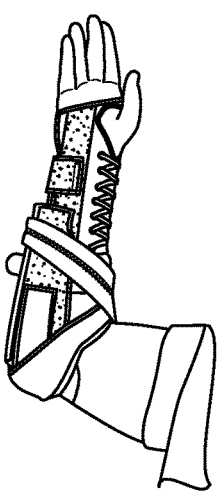

FIG. 2E. Step 5—Secure a second cross strap of the forearm wrap across the top of forearm and secure to the forearm cast or wrist splint.

Figure 2F:
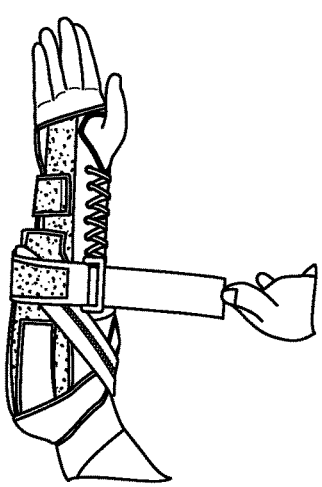

FIG. 2F. Step 6—An additional circumferential closure strap that is discrete from the forearm wrap is applied to the wrap for increased support.

It is contemplated that the patient may already be fitted with a wrist cast, short arm cast, thumb spica cast, or the like. So the patient can wear the existing cast and be fitted with the present invention sugar tong brace as described above. To do this, hook and loop fasteners or mechanical fasteners can be applied to the proximal end of the cast for attachment to the connective means 2 to minimize twisting between the two braces. This limits the amount of unwanted forearm pronation or supination. During the final stage of patient rehabilitation, the cast can be replaced with, for example, the hand-wrist orthosis shown in FIG. 1. As such, the sugar tong forearm brace is designed to be used with different step down protocols depending on the injury and treatment protocol of the practitioner or physician.

Figure 13:
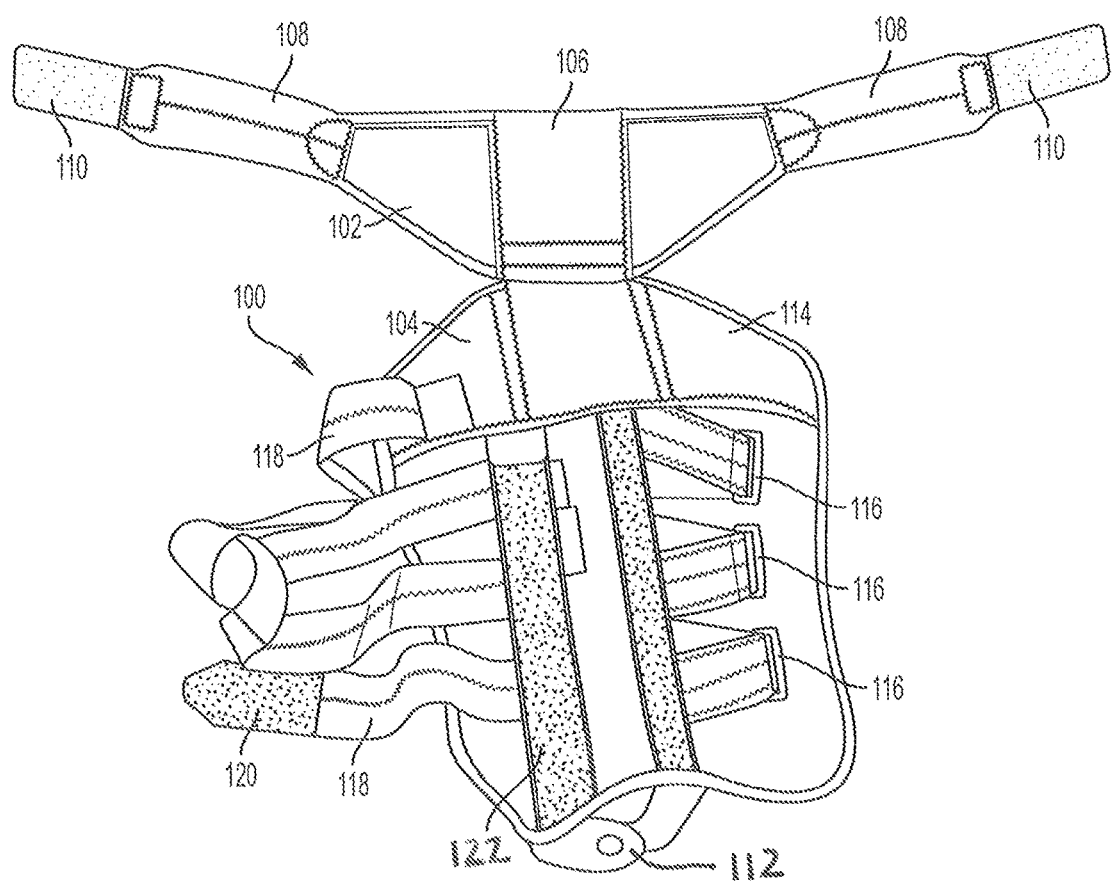
FIG. 13 shows the exterior of an alternative embodiment wrist-forearm-elbow anti-rotation support system, laid open on a flat surface.
Figure 14:
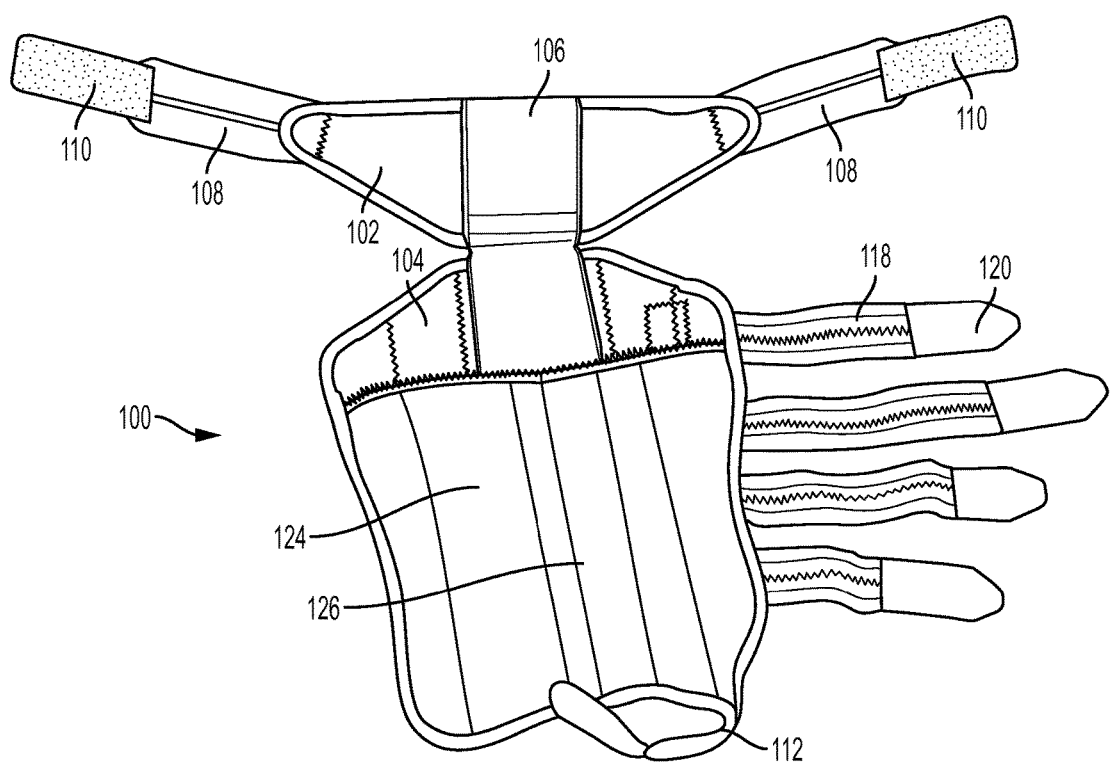
FIG. 14 shows the interior of the alternative embodiment wrist-forearm-elbow anti-rotation support system from FIG. 13.
Figure 15:
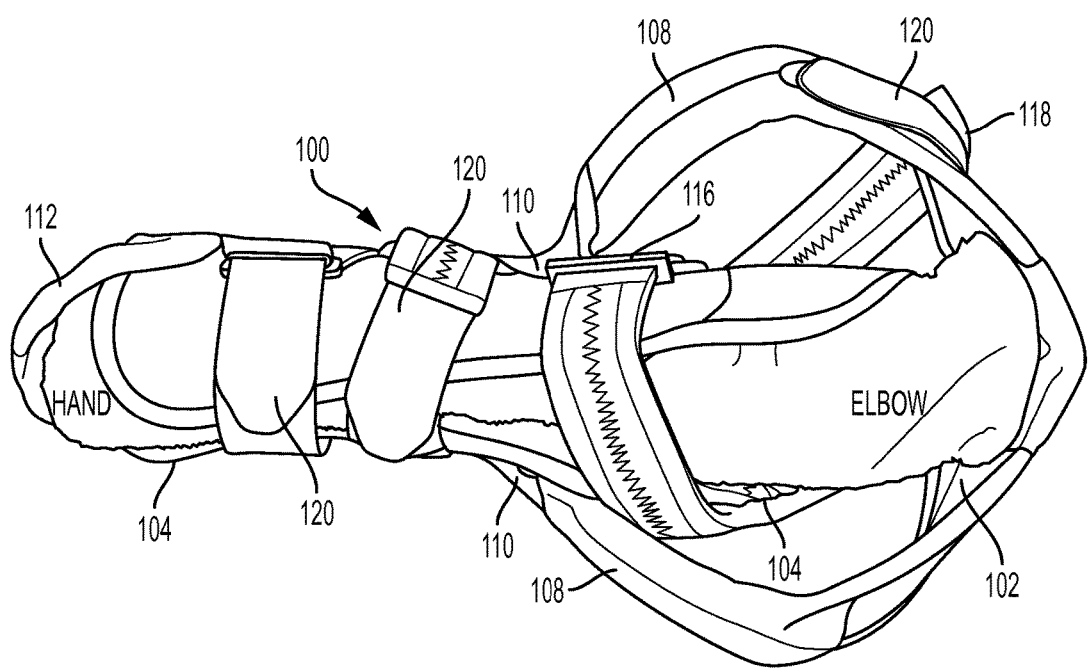
FIG. 15 shows the alternative embodiment wrist-forearm-elbow anti-rotation support system of FIG. 13 as applied to a simulated arm, represented by a rolled up towel.

FIGS. 13-15 depict an alternative embodiment wrist-forearm-elbow anti-rotation support system. The alternative embodiment one-piece sugar tong is basically the two-piece sugar tong, described above, made into one, and not requiring addition or incorporation of any hardenable material to function properly. In this embodiment, the wrist brace portion is integrated into the sugar tong/MTC splint, therefore, requiring rights and lefts for this particular embodiment. It is contemplated, however, to make a version adaptable for either the left or right arm.

Specifically, FIGS. 13 and 14 depict the exterior and interior, respectively, of a one-piece sugar tong splint 100. FIG. 15 shows the alternative embodiment as applied to a simulated arm, here a rolled up towel. The proximal end is labeled "ELBOW" and the opposite distal end is labeled "HAND" to represent the patient's hand and elbow locations when wearing the splint 100. In FIGS. 13, 14, a padded proximal wrap 102 supports the elbow of the patient while cross straps 108 with optional VELCRO® or like closures 110 allow the straps to be attached to the rest of the splint 100. The cross straps 108 extend from opposed sections of the proximal wrap 102. There is one cross strap 108 per section, but other configurations using more straps or fewer are contemplated. The cross straps 108 optionally include thicker, bulkier padding and have greater rigidity to improve the anti-rotation function of the brace 100. That is, with the more rigid cross straps 108, when applied to the arm in a crisscross fashion, with their ends being securely anchored to the rest of the splint 100, each cross strap 108 resists inadvertent forearm rotation in either direction, thus minimizing any re-injury to the patient's arm. In an alternative embodiment, the cross straps 108 do not have to crisscross when applied.

The proximal wrap 102 transitions to the forearm wrap 104 via a humeral connection 106, preferably a rectangular piece made from a soft, stretchable, flexible fabric or the like. The humeral connection 106 includes a proximal section and a distal section. The distal section is attached, preferably by stitching, to the forearm wrap 104. The proximal section is attached, preferably by stitching, to the proximal wrap 102. Instead of or in addition to stitching, the attachment may be achieved by riveting, chemical or heat bonding, or any combination thereof. It is contemplated that the humeral connection 106 may also be formed from and is an integral part of the proximal wrap 102, the forearm wrap 104, or both. In the preferred embodiment, the stretchable fabric of the humeral connection 106 accommodates many patient arms of various lengths without the doctor's office or clinic having to carry a large inventory of sizes to achieve precise fitment.

The forearm wrap 104 preferably includes opposed, medial and lateral forearm flaps 114 that when applied to the patient's forearm form a clamshell style support that at least partially circumscribes the forearm, as seen in FIG. 15. All of the stiffener inserts, stiffener pockets, padding, reinforcement, coverings, coatings, etc. described in connection with the two-piece sugar tong embodiments apply here to the forearm wrap 104 as well. Further, the forearm wrap 104 in various embodiments may be created from or include laminated sheets of ethylene vinyl acetate foam (EVA) and unbroken loop (UBL) fabric.

As best seen in FIG. 15, there is preferably a much larger gap between the upper (humeral) flap section versus the lower forearm flap section, where the material connecting the latter is a thinner fabric and more semi-flexible, and may be more thinly padded, or may not be padded at all. One reason for the larger gap is arm length accommodation. Also, the one-piece sugar tong does not have the benefit of securing over a wrist/forearm brace as in the two-piece embodiment, so more or less material may be used for reinforcement or freedom of movement, respectively.

As seen in FIG. 13, the exterior of the forearm wrap 104 preferably includes a plurality of closure straps 118 that close the clam shell, and may be routed through optional b-rings 116 so that it is easier for the patient to cinch up for a firmer, tighter wrap. VELCRO® or like closures 120 are used to secure the free ends to the exterior of the forearm flaps 114, which is partially or fully covered in VELCRO® patches or strips 122. Of course, the closures 120 instead of or in addition to VELCRO® may include hooks, claws, drawstrings, laces, snaps, buttons, eyelets, rings, zippers, or the like. The strap structure, materials, and attachments for the two-piece sugar tong embodiment may be applied here to the one-piece sugar tong splint 100.

In this embodiment, there are preferably three closure straps 118 with incrementally longer lengths moving up toward the elbow, with D-rings 116 for circumferential compression on the distal portion (forearm) of the brace 100. Thus, the strap overlying the wrist is preferably the shortest, and the longer length straps are arranged toward the elbow to accommodate the increasing girth of the upper forearm versus the wrist. There is preferably one optional assist strap 118—that being the strap closest to the elbow in the series of securement straps 118. This strap has sufficient length to circumscribe the forearm partially, fully, or multiple times, and can be applied to the arm first to hold the brace in place when initially applying the brace. The straps 118 are preferably inelastic or minimally stretchable lengthwise and/or widthwise, but elastic straps are contemplated for alternative embodiments. Leather or rubber belts and bands, laces, wire strands, and the like may be used in place of or in addition to the straps.

The interior of the forearm wrap 104 is shown in FIG. 14. The interior is padded 124 and may include pockets for further stiffener inserts, gel pads, foam or fabric padding, etc. An optional hinge or spine 126 joins the clamshell flaps 114. In one embodiment, the upper arm flaps do have a split in them like the two-piece embodiment, but not the forearm portion. It is contemplated that both the lower forearm portion and upper humeral arm portion of the forearm flaps 114 can be split, continuous, or a combination thereof.

Figure 16:
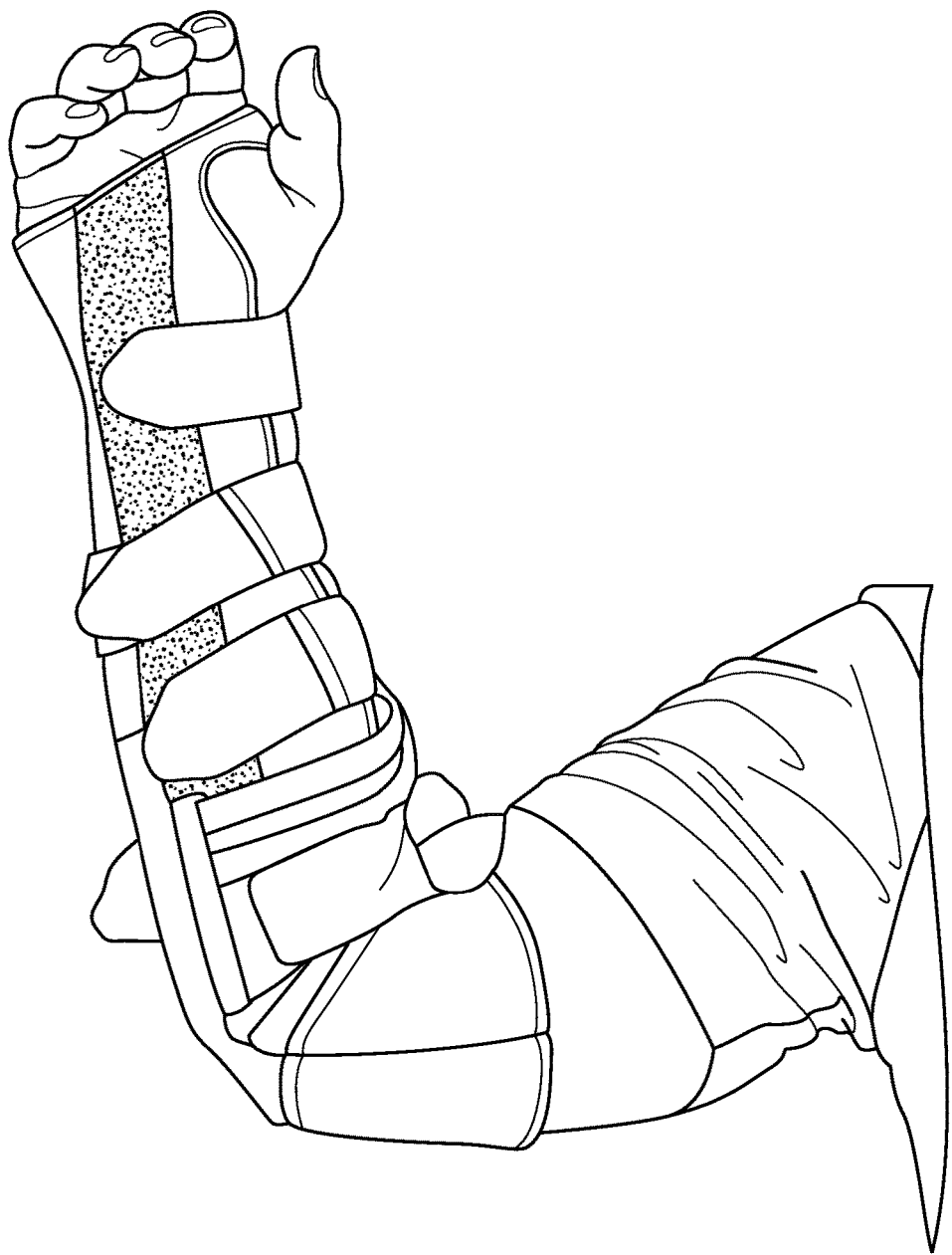
FIG. 16 shows an alternative embodiment wrist-forearm-elbow anti-rotation support system applied to and worn on the right arm.

The distal end of the forearm wrap 104 labeled "HAND" in FIG. 15 includes a web space closure, strap, or the like 112. The preferred closure strap 112 is shaped as described above in connection with the two-piece sugar tong splint, and extends from one of the clamshell flaps 114 and attaches to the other as seen in FIGS. 15 and 16. The attachment is accomplished by VELCRO® or any attachment means known in the art. In the left-arm embodiment of the one-piece sugar tong 100 shown in FIGS. 13-15, the web space closure 112 extends from the portion of the clamshell flap 114 covering the patient's dorsum of the hand passing over the web of the hand and attaching to the clamshell flap 114 covering the palm region of the hand. The web space closure 112 is made preferably from the same material as the forearm wrap near the wrist area. In FIG. 13, the web space closure 112 is depicted as a padded strap extending from one of the clamshell flaps 114 to the other, with a narrow section that overlies the web of the hand. The web space closure in an alternative embodiment may include a thumb spica as described above to immobilize the thumb.

One or more rigid or semi-rigid inserts, whether metal or plastic strips or rods, etc., may be embedded in the wrist area of the flaps 114 to further limit rotation of the wrist. The metal strips may have a pre-formed curvature to follow the curvature of the patient's wrist, hand, arm, or elbow anatomy. FIG. 16 shows an alternative embodiment wrist-forearm-elbow anti-rotation support system applied to and worn on the right arm.

It is contemplated that an alternative embodiment wrist-forearm-elbow anti-rotation brace/system does not require a left- or right-side specific splint, but one that would simply apply to either arm and all the straps could be reversible. However, it is an advantage having the wrist brace left- or right-side specific makes for a much quicker and form fitting application for the wearer or patient.

While particular forms of the invention have been illustrated and described, it will be apparent that various modifications can be made without departing from the spirit and scope of the invention. It is contemplated that disclosed embodiments and their components may be combined with other disclosed embodiments and their components.

What is claimed is:

1. A wrist-forearm-elbow anti-rotation support system that does not include a hardenable material, comprising:
   a forearm wrap having a proximal end and a distal end, the forearm wrap including two opposed, first and second forearm flaps wrapped into a clamshell form, wherein the flaps approach each other, and wherein the first and second forearm flaps are discrete flaps joined along a common edge by a soft sheet of fabric;
   a humeral connection having a proximal section and a distal section, wherein the distal section connects to the forearm wrap;
   proximal elbow flaps extending from the proximal section;
   first and second straps extending from the proximal elbow flaps that attach to the first and second forearm flaps; and
   a web space closure disposed at the distal end of the forearm wrap, and extending from the first forearm flap to the second forearm flap.

2. The wrist-forearm-elbow anti-rotation support system of claim 1, a third strap extending from an edge of the first forearm flap and overlying where the first and second forearm flaps approach each other to join the opposed second forearm flap.

3. The wrist-forearm-elbow anti-rotation support system of claim 2, wherein the system includes fourth, fifth, and sixth straps spaced apart along the forearm wrap.

4. The wrist-forearm-elbow anti-rotation support system of claim 3, wherein the straps have incrementally longer lengths moving from the distal end to the proximal end of the forearm wrap.

5. The wrist-forearm-elbow anti-rotation support system of claim 1, wherein the first and second straps include thick padding and crisscross when applied.

6. The wrist-forearm-elbow anti-rotation support system of claim 1, wherein the first and second forearm flaps include a plurality of semi-rigid panels.

7. The wrist-forearm-elbow anti-rotation support system of claim 1, wherein at least one of the forearm flaps proximate the distal end of the forearm wrap includes a rigid stiffener embedded therein.

8. The wrist-forearm-elbow anti-rotation support system of claim 1, wherein at least one of the first and second forearm flaps includes an internal stiffener.

9. A method for applying a wrist-forearm-elbow anti-rotation support system to a patient's thumb, wrist, forearm, or elbow, without use of a hardening material, comprising:
   providing a forearm wrap with opposed first and second forearm flaps wrapped into a clamshell form wherein the flaps approach each other, and wherein the forearm wrap includes a distal end and a proximal end;
   embedding stiffeners into the forearm wrap;
   applying the forearm wrap to the patient's forearm;
   providing a humeral connection extending from the proximal end of the forearm wrap, wherein proximal elbow flaps extend from the humeral connection, and the proximal flaps include first and second straps;
   inserting the patient's elbow into at least one of the humeral connection and proximal elbow flaps;
   securing the first and second straps to the forearm wrap;
   providing a third strap and a fourth strap, extending from the first to the second forearm flap, wherein the fourth strap is located proximate the distal end at the patient's wrist;
   anchoring the third and fourth straps to the second forearm flap;
   providing a web space closure at the distal end of the forearm wrap, extending from the first forearm flap to the second forearm flap; and
   applying the web space closure to the second forearm flap.

10. A wrist-forearm-elbow anti-rotation support system that does not include a hardenable material, comprising:
    a forearm wrap with two opposed, first and second forearm flaps creating a clamshell form, wherein the wrap includes a distal end and a proximal end;
    a stiffener embedded within the first forearm flap proximate the distal end;
    a humeral connection extending from the proximal end of the forearm wrap; proximal elbow flaps extending from the humeral connection, wherein the proximal elbow flaps include first and second straps that attach to the forearm wrap;
    a third strap extending from the first forearm flap to the second forearm flap closing the clamshell form;
    a fourth strap positioned proximate the distal end of the forearm wrap, extending from the first forearm flap to the second forearm flap closing the clamshell form and compressing of the forearm wrap; and
    a web space closure disposed at the distal end of the forearm wrap, extending from the first forearm flap and anchored to the second forearm wrap.

11. The wrist-forearm-elbow anti-rotation support system of claim 10, wherein the system includes a fifth assist strap at least partially disposed about a circumference of the forearm wrap.

12. The wrist-forearm-elbow anti-rotation support system of claim 11, wherein the connective means includes a hook component of a hook and loop fastener.

13. The wrist-forearm-elbow anti-rotation support system of claim 11, wherein the plurality of stiffeners embedded within the forearm wrap extend substantially the entire length of the forearm wrap.

14. The wrist-forearm-elbow anti-rotation support system of claim 10, wherein an exterior of the forearm wrap includes unbroken loop fabric.

15. The wrist-forearm-elbow anti-rotation support system of claim 10, wherein the forearm wrap includes laminated sheets of ethylene vinyl acetate foam (EVA) and unbroken loop (UBL) fabric.

16. The wrist-forearm-elbow anti-rotation support system of claim 10, wherein the proximal elbow flaps include first and second straps that attach to the forearm wrap in a crisscross arrangement.

17. The wrist-forearm-elbow anti-rotation support system of claim 10, wherein the humeral connection includes a soft, stretchable fabric.

* * * * *